United States Patent
Xu et al.

(10) Patent No.: US 9,716,001 B2
(45) Date of Patent: Jul. 25, 2017

(54) METHOD FOR ANALYZING IONIC STRUCTURE

(71) Applicant: BEIJING INSTITUTE OF TECHNOLOGY, Beijing (CN)

(72) Inventors: Wei Xu, Beijing (CN); Muyi He, Beijing (CN); Xiang Fang, Beijing (CN)

(73) Assignee: BEIJING INSTITUTE OF TECHNOLOGY, Beijing (CN)

( * ) Notice: Subject to any disclaimer, the term of this patent is extended or adjusted under 35 U.S.C. 154(b) by 0 days.

(21) Appl. No.: 14/430,533

(22) PCT Filed: Sep. 5, 2014

(86) PCT No.: PCT/CN2014/086049
§ 371 (c)(1),
(2) Date: Mar. 23, 2015

(87) PCT Pub. No.: WO2016/033807
PCT Pub. Date: Mar. 10, 2016

(65) Prior Publication Data
US 2016/0247670 A1    Aug. 25, 2016

(51) Int. Cl.
*G01N 27/62* (2006.01)
*H01J 49/42* (2006.01)
(Continued)

(52) U.S. Cl.
CPC .......... *H01J 49/422* (2013.01); *H01J 49/005* (2013.01); *H01J 49/427* (2013.01); *G01N 27/68* (2013.01)

(58) Field of Classification Search
CPC ...... H01J 49/005; H01J 49/027; H01J 49/422; H01J 49/424; H01J 49/24; G01N 27/622; G01N 27/624
See application file for complete search history.

(56) References Cited

U.S. PATENT DOCUMENTS

2004/0195502 A1    10/2004   Hashimoto et al.
2008/0128610 A1     6/2008   McLuckey et al.
(Continued)

FOREIGN PATENT DOCUMENTS

CN          103871820          6/2014

OTHER PUBLICATIONS

Xu, Wei, et al. "Nondestructive ion trap mass analysis at high pressure." Analytical chemistry 83.3 (2010): 685-689.*

(Continued)

*Primary Examiner* — Wyatt Stoffa
(74) *Attorney, Agent, or Firm* — WPAT, P.C., Intellectual Property Attorneys; Anthony King

(57) ABSTRACT

A method for analyzing ionic structure, including: applying a radio frequency electric field on an ion mass analyzer to cause sample ions to be excited to a motion amplitude, the motion amplitude at this moment being recorded as a primary motion amplitude; continuously feeding carrier gas into the ion mass analyzer and keeping a certain degree of vacuum in the ion mass analyzer, the sample ions being collided with the carrier gas and the motion amplitude being decreased gradually, and collecting a time domain signal of an image current generated by the sample ions during the process; and analyzing the time domain signal through a time-frequency analysis method and obtaining time-varying characteristic curves indicating corresponding relations between the motion frequencies of the ions having corresponding sizes and the collision cross sectional areas of the ions and the carrier gas, thus distinguishing among ions having different sizes.

8 Claims, 4 Drawing Sheets

(51) Int. Cl.
*H01J 49/00* (2006.01)
*G01N 27/68* (2006.01)

(56) References Cited

U.S. PATENT DOCUMENTS

2009/0179149 A1   7/2009  Sugiyama et al.
2015/0262801 A1*  9/2015  Xu .................... H01J 49/0036
                                                                    702/27
2015/0276676 A1  10/2015  Jiang et al.

OTHER PUBLICATIONS

Wang, Yuzhuo, et al. "The coupling effects of hexapole and octopole fields in quadrupole ion traps: a theoretical study." Journal of Mass Spectrometry 48.8 (2013): 937-944.*

He, Muyi, et al. "Ion collision crosssection measurements in quadrupole ion traps using a time-frequency analysis method." Analyst 139.23 (2014): 6144-6153.*

Office Action dated Nov. 21, 2016 for the China counterpart application 201480001235.0 from the State Intelletual Property Office.

English abstract translation of the Office Action dated Nov. 21, 2016 for the China counterpart application 201480001235.0 from the State Intelletual Property Office.

Fan Yang et al., "Collision Cross Sectional Areas form Analysis of Fourier Transform Ion Cyclotron Resonance Line Width: A New Method for Characterizing Molecular Structure," Analytical Chemistry, vol. 84, pp. 4851-4857.

US patent published application 2015/0276676A1 serves as a translation for the reference CN 103871820.

* cited by examiner

METHOD FOR ANALYZING IONIC STRUCTURE

RELATED APPLICATION

The present application is a Continuation Application of International Application PCT/CN2014/086049, with an international filing date of Sep. 5, 2014, which is incorporated by reference in its entirety.

TECHNICAL FIELD

The present disclosure relates to a method for analyzing ionic structure, and more particularly, to a method which can be applied to a Fourier transform equipment, and analyze an ionic structure through determination of collision cross sectional areas.

BACKGROUND

Mass spectrometry refers to an analysis method that separates and detects compounds by different mass-to-charge ratios (m/z) to implement component and structure identification. The mass spectrometry technique has become increasingly prominent in the field of bioanalysis due to its high specificity and sensitivity. Bio-mass spectrometry (Bio-MS) is a mass spectrometry technique applied to analyze biomolecules, which is widely applied in protein and polypeptide researches such as relative molecular mass determination of protein, peptide mapping determination, peptide sequence determination technique, assignment of sulfhydryl and disulfide bond, posttranslational modification of protein, quantitative proteome analysis, protein-protein interaction research, and the like. Moreover, the bio-mass spectrometry is also applied to such fields as polysaccharose structure determination, oligonucleotide and nucleic acid analysis, microorganism identification, medicament research and development and the like.

The mass spectrometry can obtain the mass information of samples, but cannot give more information effectively for different samples having the same mass. For example, it is different to analyze an ionic structure via the mass spectrometry. Currently, ionic structures are generally analyzed through tandem mass spectrometry (tandem MS) and ion mobility spectrometry. The tandem MS applies energy to fragment an ion to be determined, and analyzes the fragment ion to reconstruct the ionic structure, while the ion mobility spectrometry analyzes the collision cross sectional area of the ion to be determined to analyze the ionic structure. The tandem MS usually works under a high vacuum condition (<1 mTorr), while the ion mobility spectrometry works under a high pressure condition (>1 Torr) and has lower resolution (usually lower than 1,000). These methods require a complicated instrument structure and increased vacuum consumption due to the big difference between the working pressures. Meanwhile, experimental control conditions for the ion to be determined are harsh and ion loss is significant since migration movement of the ion between a plurality of vacuum cavities is involved.

In 2012, Fan Yang, Jacob E. Voelkel and David V. Dearden proposed to analyze collision cross sectional areas of ions from analysis of Fourier transform ion cyclotron resonance spectrum line width so as to analyze the ionic structure in "Collision Cross Sectional Areas from Analysis of Fourier Transform Ion Cyclotron Resonance Line Width: A New Method for Characterizing Molecular Structure" (Anal. Chem., 2012, 84 (11), pp 4851-4857). The method increases the pressure inside a Fourier transform ion cyclotron resonance ion trap to decay an image current of a dominant ion for ion-molecule collision. The rate of decay determines the half peak width (full width at half maximum, FWHM) of the spectrum line. The faster the rate of decay in time domain is, the wider the half peak in corresponding frequency domain is. The ion collision area can be calculated by measuring the half peak width, so that the ion collision area may be analyzed through the decay of the image current of the ion, and finally the ionic structure may be obtained.

Moreover, conventional ion mobility spectrometry can obtain the space size information of the samples, i.e. detect the collision cross sectional area (CCS) of the samples, while obtaining the mass of the samples, and then effectively identity various isomers having the same mass. However, the ion mobility spectrometry increases the analysis cost and reduces the analysis efficiency.

SUMMARY

In order to at least partially solve the foregoing problems, the present disclosure provides a method for analyzing ionic structure which can analyze an ionic structure by analyzing a time-frequency signal of an ion to be measured from an ion mass analyzer.

According to an aspect of the present disclosure, there is provided a method for analyzing ionic structure, including the following steps.

Ion trapping and exciting step: applying a radio frequency electric field on an ion mass analyzer to trap sample ions in the ion mass analyzer, the applied radio frequency electric field having a high order component; and applying an auxiliary alternating current electric field or applying a broadband excitation electric field on the ion mass analyzer to cause the sample ions to be excited to a motion amplitude not exceeding the trapping ability of the ion mass analyzer, the motion amplitude at this moment being recorded as a primary motion amplitude and the moment corresponding to the primary motion amplitude being recorded as a first moment.

Signal collecting step: continuously feeding carrier gas into the ion mass analyzer and keeping a degree of vacuum in the ion mass analyzer to be smaller than 1.333 Pa, the sample ions being collided with the carrier gas and the motion amplitude being decreased gradually till a second moment, and collecting a time domain signal of an image current generated by the sample ions during the process from the first moment to the second moment.

Signal processing step: analyzing the time domain signal through a time-frequency analysis method and respectively obtaining time-varying characteristic curves of the motion frequencies of ions having various sizes in the sample ions varied with time so as to distinguish among the ions having different sizes, each of the time-varying characteristic curves indicating a corresponding relation between the motion frequency of the ion having a corresponding size and the collision cross sectional area of the ion and the carrier gas.

According to an embodiment of the present disclosure, after the signal processing step, the method further includes a time domain signal filtering step: the time domain signal being filtered by a filter so as to obtain a less-interfered time domain signal.

According to an embodiment of the present disclosure, the time-frequency analysis method in the signal processing step is selected from Fourier transform method, fast Fourier transform method, short time Fourier transform method, fractional Fourier transform method or wavelet analysis method.

According to an embodiment of the present disclosure, in the signal processing step, the time-varying characteristic curve of the motion frequency (f) of the sample ion varied with time satisfies equation:

$$f = f_0 \sqrt{1 + \frac{3a_1^2}{4}\epsilon_3 + \frac{5a_1^4}{8}\epsilon_5 + \frac{35a_1^6}{64}\epsilon_7 + \ldots} \quad (1)$$

where $a_1$ is the motion amplitude of the sample ion; $f_0$ is the motion frequency of the ion without a high order field; and $\epsilon_3$, $\epsilon_5$ and $\epsilon_7$ are even order field perturbation coefficients, and $$a_1 = \frac{1}{(1/a_0 + c)e^{\frac{\delta_1}{2}t} - c} \quad (2)$$

where $a_0$ is the primary motion amplitude of the sample;

$$c = \frac{8\delta_2 \omega_0}{3\pi\delta_1}$$

is a constant;

$$\delta_1 = \frac{q\sqrt{\frac{\alpha_p(M+m)}{mM}}}{2\varepsilon_0} \frac{p}{Tk} \frac{M}{m+M}$$

is a Langevin decay coefficient;

$$\delta_2 = (\pi r^2) \frac{p}{Tk} \frac{M}{m+M}$$

is a hard-sphere decay coefficient; r is the effective radius of the sample ion; q is the charge of the sample ion; $\alpha_p$ is a polarizability; $\epsilon_0$ is a permittivity of vacuum; p is a degree of vacuum; T is a thermodynamic temperature; k is a Boltzmann constant; M is the mass of the carrier gas; and m is the mass of the sample ion;

substituting equation (2) into equation (1), thus obtaining a relation equation of the effective radius of the sample ion and the motion frequency of the sample ion varied with time.

According to an embodiment of the present disclosure, the method further includes the following step of:

drawing a relation curve of the effective radius of the sample ion and the motion frequency of the sample ion varied with time through a numerical method according to the relation equation of the effective radius of the sample ion and the motion frequency of the sample ion varied with time.

According to an embodiment of the present disclosure, the method further includes a signal analysis step:

obtaining corresponding characteristic values by analyzing each time-varying characteristic curve from the signal processing step, and establishing a corresponding relation between each characteristic value and the collision cross sectional area of the ion having the corresponding size, thus determining a size relation between the ions having various sizes in the sample ions.

According to an embodiment of the present disclosure, in the signal analysis step, with respect to each time-varying characteristic curve, the characteristic value thereof is obtained through a following step:

connecting a motion frequency point of the sample ion at the first moment with a motion frequency point of the sample ion at the second moment to create a straight line, and integrating over a closed curve encircled by the straight line and the time-varying characteristic curve from the first moment to the second moment to obtain the characteristic value of the time-varying characteristic curve.

According to an embodiment of the present disclosure, in the signal processing step, the time-varying characteristic curve of the motion frequency varied with time satisfies equation:

$$f = f_0 \sqrt{1 + \frac{3a_1^2}{4}\epsilon_3 + \frac{5a_1^4}{8}\epsilon_5 + \frac{35a_1^6}{64}\epsilon_7 + \ldots} \quad (1)$$

where $a_1$ is the motion amplitude of the sample ion; $f_0$ is the motion frequency of the ion without a high order field; and $\epsilon_3$, $\epsilon_5$ and $\epsilon_7$ are even order field perturbation coefficients, and $$a_1 = \frac{1}{(1/a_0 + c)e^{\frac{\delta_1}{2}t} - c} \quad (2)$$

where $a_0$ is the primary motion amplitude of the sample;

$$c = \frac{8\delta_2 \omega_0}{3\pi\delta_1}$$

is a constant;

$$\delta_1 = \frac{q\sqrt{\frac{\alpha_p(M+m)}{mM}}}{2\varepsilon_0} \frac{p}{Tk} \frac{M}{m+M}$$

is a Langevin decay coefficient;

$$\delta_2 = (\pi r^2) \frac{p}{Tk} \frac{M}{m+M}$$

is a hard-sphere decay coefficient; $r_0$ is the effective radius of the sample ion; q is the charge of the sample ion; $\alpha_p$ is a polarizability; $\epsilon_0$ is a permittivity of vacuum; p is a degree of vacuum; T is a temperature; k is a Boltzmann constant; M is the mass of the carrier gas; and m is the mass of the sample ion;

substituting equation (2) into equation (1), thus obtaining a relation equation of the effective radius of the sample ion and the motion frequency of the sample ion varied the time; and under a same measuring condition, respectively integrating over time on both sides of the relation equation of the frequency and the effective radius of the sample ion, thus obtaining a corresponding relation between a characteristic value S and the effective radius of the ion having a corresponding size.

In the method for analyzing ionic structure according to the present disclosure, there is provided a collision cross sectional area determination method based on a Fourier transform equipment and time-frequency analysis, which enables ionic structure analysis, can be widely applied in an equipment based on Fourier transform, expands the detection ability of the Fourier transform equipment, and realizes non-destructive testing of the space size information of the sample ions. Based on the exact determination with respect to the space sizes of the sample ions, isomers such as different conformations of the same protein can be distinguished, or complicated mixed samples having the same mass but different sizes can be detected through this method at a time, thus the detection efficiency of the sample ions is improved, and the detection cost is reduced.

BRIEF DESCRIPTION OF THE DRAWINGS

The accompanying drawings provide further understanding of the invention, illustrate embodiments consistent with the invention and, together with the description, serve to explain the principles of the invention. In the accompanying drawings.

DETAILED DESCRIPTION OF THE INVENTION

The embodiments of the invention will be described in detail with reference to the accompanying drawings. It will be appreciated that the embodiments are only exemplary embodiments, and not intended to limit the present invention.

Referring to FIG. 1 to FIG. 4, in a method for analyzing ionic structure according to an embodiment of the present disclosure, sample ion parameters: the sample ions include at least two isomer samples having a mass-to-charge ratio of 524 (m/z), which are respectively a big ion and a small ion, and wherein the size of the small ion (indicated by the effective radius r1 of the small ion) r1=0.883 nm and a collision cross sectional area is $\pi(r1)^2$; the size of the big ion (indicated by the effective radius r2 of the small ion) r2=2.883 nm and a collision cross sectional area is $\pi(r2)^2$. The method includes the steps as follows.

Figure 1:
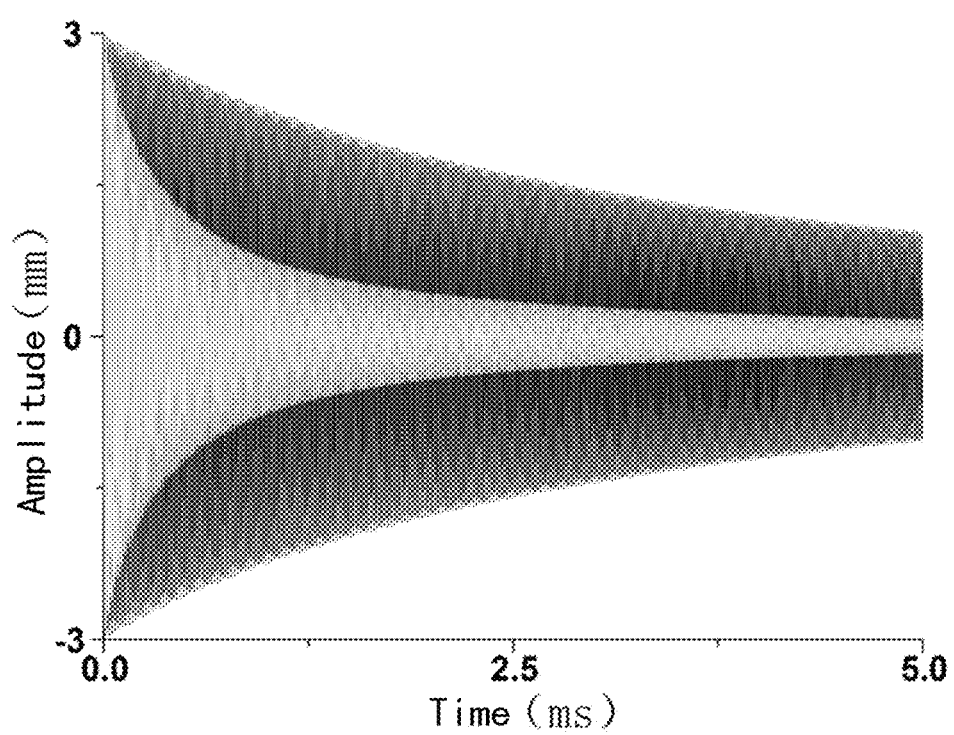
FIG. 1 shows a motion decay curve of two isomers under a simulation condition, i.e. an intensity decay curve of an image current.

Ion trapping and exciting step: a radio frequency electric field (RF) is applied on an ion mass analyzer in which there is a linear ion trap, for example, having a physical size of 5×5 mm and a distance from an electrode to the center of the trap is 5 mm; the radio frequency electric field applied has a high order component, and the high order component of the field may be obtained through a manner such as changing the shape of the electrode, so that sample ions are trapped in the linear ion trap; the frequency of the radio frequency electric field is 1 MHz, the amplitude of the radio frequency electric field is 400 V, and the q value of the radio frequency electric field is 0.3; moreover, an auxiliary alternating current electric field AC is applied on the 5×5 mm linear ion trap, so that the big and small ions of the sample ions are excited to a same motion amplitude not exceeding the trapping capacity of the linear ion trap, the motion amplitude being recorded as a primary motion amplitude $a_0$ at this moment. The auxiliary alternating current electric field AC for exciting the sample ions may also be replaced by a broadband excitation electric field SWIFT. As shown in FIG. 1, the motion of the sample ions trapped in the 5×5 mm linear ion trap may be described by using a Mathieu equation; after carrier gas is fed, the ions are collided with neutral gas and energy exchange occurs, so that the motion amplitude of the ions would decrease gradually from the primary motion amplitude $a_0$. As shown in FIG. 1, the primary motion amplitude $a_0$ is 3 mm, and the moment corresponding to the primary motion amplitude $a_0$ is recorded as a first moment $t_0$.

The 5×5 mm linear ion trap in the step may also be replaced by other ion mass analyzers.

Signal collecting step: helium is continuously fed into the 5×5 mm linear ion trap and served as the carrier gas, a degree of vacuum in the linear ion trap is kept at 0.1333 Pa (1 mTorr), and the motion amplitude of the sample ion is gradually decreased from the primary motion amplitude $a_0$; as the decay process shown in FIG. 1, a signal collecting time from the first moment $t_0$ to a second moment tt is 5 ms; and a time domain signal of an image current produced by the sample ion during the process is collected. The helium may also be replaced by nitroge or other gases that are suitable to be served as the carrier gas.

Filtering step: the time domain signal obtained in the foregoing step is filtered twice by a low pass filter until a less-interfered time domain signal is obtained. The filter may also be configured with a band pass filter and the like.

Figure 2:
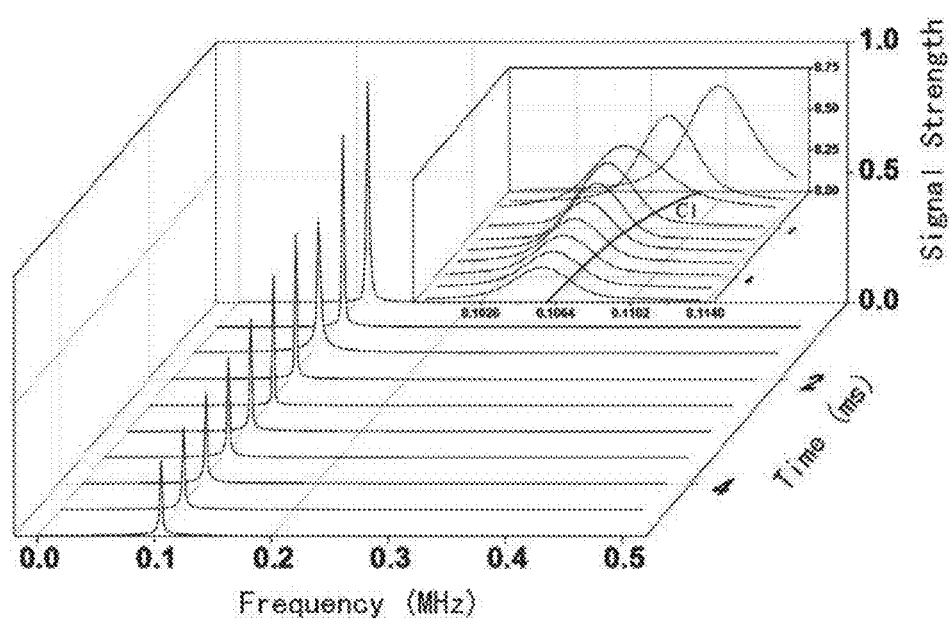
FIG. 2 shows a time-frequency mass spectrogram obtained by performing time-frequency analysis on a time domain signal of one from the two isomers shown in FIG. 1.
Figure 3A:
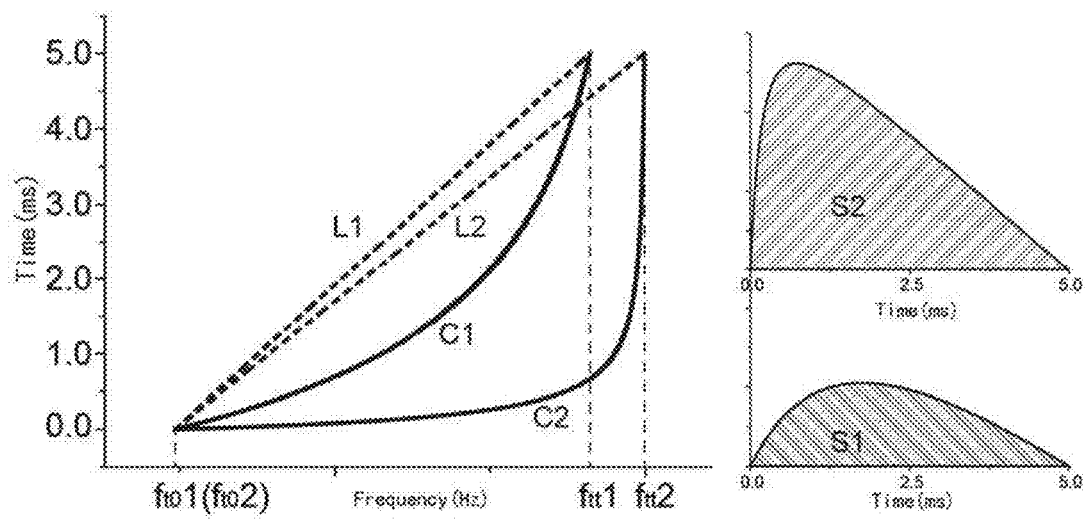
FIG. 3a shows time-frequency curves of the two isomers shown in FIG. 1.

Signal processing step: referring to FIG. 2 and FIG. 3a, the forgoing time domain signal is analyzed through a short time Fourier transform (STFT) method to obtain a time-varying characteristic curve C1 indicating the motion frequency $f_1$ of the small ion in the sample ions varied with time and a time-varying characteristic curve C2 indicating the motion frequency $f_2$ of the big ion varied with time, respectively; the time-varying characteristic curve C1 of the small ion includes a corresponding relation between the motion frequency of the small ion and the collision cross sectional area between the small ion and the carrier gas, and the time-varying characteristic curve C2 of the big ion includes a corresponding relation between the motion frequency $f_2$ of the big ion and the collision cross sectional area between the big ion and the carrier gas; therefore, the big ion and the small ion can be distinguished by identifying different motion frequency information. Ions having other sizes or other isomers in the sample ions may be distinguished similarly.

The small ion (light color portion in the middle) is taken as an example hereinafter to illustrate how to obtain the time-varying characteristic curve C1. Referring to FIG. 2, in a 5×5 mm linear ion trap, the motion frequencies of the sample ions may be different under different motion amplitudes due to such reasons as a undesirable quadrupole field, an inhomogeneous magnetic field and the like; after being transformed through short time Fourier transform, a continuous frequency variation diagram which is namely a time-frequency mass spectrogram may be obtained. Apparent center frequency deviation may be observed by amplifying a peak value portion. The curve of the motion frequency of the small ion varied with time which is namely the time-frequency curve C1 may be obtained by connecting the center frequencies of each frequency. The time-frequency curve C1 in an xy plane is as shown by C1 in FIG. 3.

In the signal processing step, the short time Fourier transform method (STFT) may also be replaced by other time-frequency analysis methods such as Fourier transform method (FT), fast Fourier transform method (FFT), fractional Fourier transform method or wavelet analysis method and the like. Further, in the signal processing step, the time-varying characteristic curve C1 of the motion frequency $f_1$ of the small ion varied with time satisfies following equation:

$$f_1 = f_0 \sqrt{1 + \frac{3a_1^2}{4} \epsilon_3 + \frac{5a_1^4}{8} \epsilon_5 + \frac{35a_1^6}{64} \epsilon_7 + \ldots} \quad (1)$$

where $a_1$ is the motion amplitude of the sample ion; $f_0$ is the motion frequency of the ion without a high order field; and $\epsilon_3$, $\epsilon_5$ and $\epsilon_7$ are even order field perturbation coefficients, and $$a_1 = \frac{1}{(1/a_0 + c)e^{\frac{\delta_1}{2}t} - c} \quad (2)$$

where $a_0$ is the primary motion amplitude of the sample;

$$c = \frac{8\delta_2 \omega_0}{3\pi \delta_1}$$

is a constant;

$$\delta_1 = \frac{q\sqrt{\frac{\alpha_p(M+m)}{mM}}}{2\varepsilon_0} \frac{p}{Tk} \frac{M}{m+M}$$

is a Langevin decay coefficient;

$$\delta_2 = \pi(r1)^2 \frac{p}{Tk} \frac{M}{m+M}$$

is a hard-sphere decay coefficient; r1 is the effective radius of the sample ion; q is the charge of the sample ion; $\alpha_p$ is a polarizability; $\epsilon_0$ is a permittivity of vacuum; p is a degree of vacuum; T is a thermodynamic temperature with a unit of Kelvin; k is a Boltzmann constant; M is the mass of the carrier gas; and m is the mass of the sample ion.

Equation (2) is substituted into equation (1), thus obtaining a relation equation of the effective radius r1 of the small ion and the motion frequency f1 of the small ion varied with time, and further obtaining a corresponding relation between the frequency f1 and the collision cross sectional area σ1 of the small ion according to a formula $\sigma_1 = \pi(r1)^2$. Further, a relation curve of the effective radius r1 of the small ion and the motion frequency f1 of the small ion varied with time is drawn through a numerical method according to the relation equation of the effective radius r1 of the small ion and the motion frequency f1 of the small ion varied with time. Similarly, a relation equation of the effective radius r2 of the big ion and the motion frequency f2 of the big ion varied with time, and a relation curve of the effective radius r2 of the big ion and the motion frequency f2 of the big ion varied with time may be obtained.

The two isomers consisting of the big ion and the small ion as well as ions and isomers having other sizes included in the sample ions can be distinguished by using the method according to the present disclosure and through the foregoing ion trapping and exciting step, filtering step, signal collecting step and signal processing step. To further identify the relation between the isomers and ions, for example, size scale and the like thereof, the method according to the present disclosure may further include a signal analysis step: obtaining corresponding characteristic values S by analyzing time-varying characteristic curves of each isomer and ions having different sizes in the signal processing step, and establishing a corresponding relation between each characteristic value S and the collision cross sectional area of the corresponding isomer and ion having different sizes, thus determining a size scale relation.

The characteristic value of the time-varying characteristic curve with respect to the small ion is obtained through a method as follows.

Figure 3B:
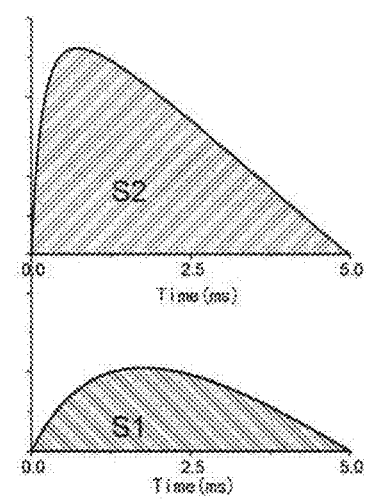
FIG. 3b shows characteristic values obtained by processing the time-frequency curves of the two isomers shown in FIG. 1.

As shown in FIG. 3a and FIG. 3b, the motion frequency point ft01 of the small ion at the first moment t01 is connected with the motion frequency point ftt1 of the small ion at the second moment tt1 to create a straight line L1, and a closed curve encircled by the straight line L1 and the time-varying characteristic curve C1 is integrated over from the first moment t01 to the second moment tt1 to obtain the characteristic value S1 of the time-varying characteristic curve of the small ion. According to the same method, the motion frequency point ft02 of the big ion at the first moment t02 is connected with the motion frequency point ftt2 of the big ion at the second moment tt2 to create a straight line L2, and a closed curve encircled by the straight line L2 and the time-varying characteristic curve C2 is integrated over from the first moment t02 to the second moment tt2 to obtain the characteristic value S2 of the time-varying characteristic curve of the big ion. The characteristic values of ions and isomers having other sizes may be obtained similarly.

A corresponding relation between the characteristic value and the collision cross sectional area may be established through the method as follows.

Figure 4:
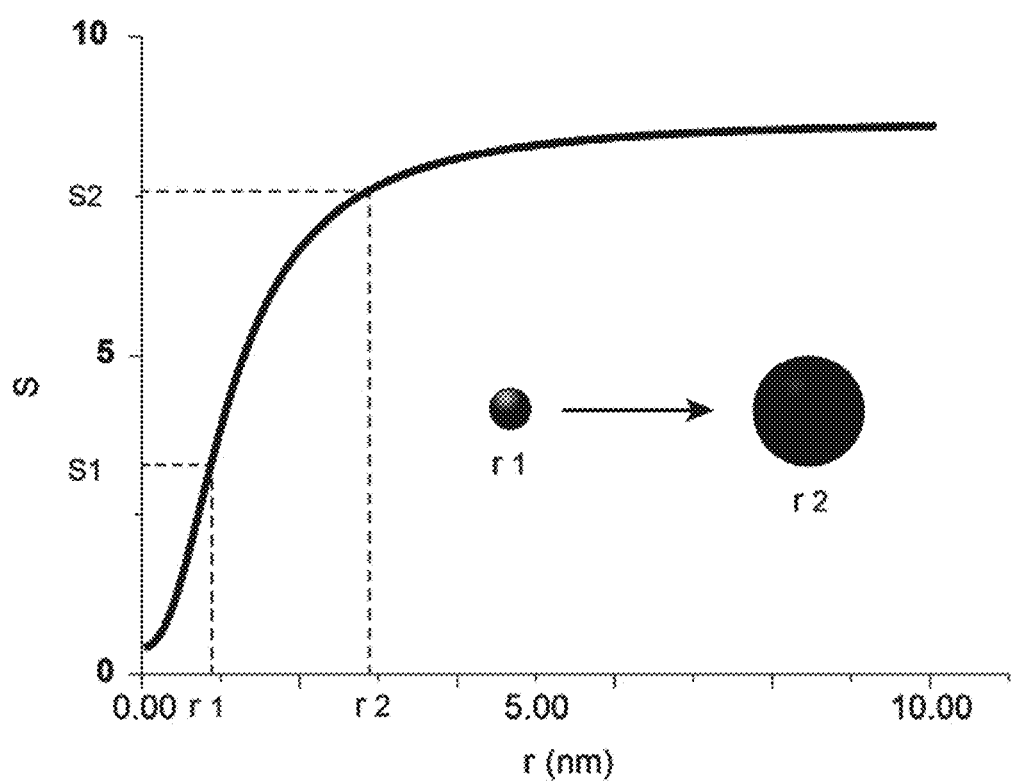
FIG. 4 shows a curve of a corresponding relation between the characteristic values and effective radius of the isomer.

As shown in FIG. 4, time is integrated over on both sides of the equal sign of the relation equation involving the effective radius of the ion and the motion frequency of the sample ion varied with time obtained in the foregoing signal processing step, so as to obtain a corresponding relation between a characteristic value S of the isomer or ions having different sizes and the effective radius of the ion; and a curve is further drawn through the numerical method. The curve is uniquely determined under the foregoing measurement conditions, the characteristic value S of any ion is measured according to the foregoing method under the same condition, and the value of the effective radius r of the ion is obtained according to the corresponding point of the characteristic value S on the curve. For example, the effective radiuses of the ions corresponding to the characteristic values S1 and S2 of two ions are r1 (0.8 nm) and r2 (2.8 nm); therefore, it can be calculated that r2=3.5 r1, and then a size scale relation of the two ions can be calculated. Under the same test conditions, the exact value of the effective radius of the sample ion may be obtained by measuring the characteristic values of unknown sample ions. From the document of Fan Yang, Jacob E. Voelkel and David V. Dearden, the effective radiuses r1 and r2 of the ions may correspond to the collision cross sectional area of the ions and the carrier gas; therefore, the exact value of the collision cross sectional area of the sample ion may be obtained by measuring the characteristic values of the unknown sample ions.

It should be noted that methods for creating the characteristic values are not exclusive. Rather, it may be feasible to obtain the characteristic values such as area, slope and radius of curvature through the time-frequency curves of ions by means of methods such as integral, differentiation and the like.

The method for analyzing ionic structure according to the present disclosure can be employed to quickly identify different isomers or ions having same mass but different space sizes in the sample ions, and exactly determine the scale relation between the effective radiuses of those isomers or ions having differentiation sizes.

INDUSTRIAL APPLICABILITY

In the method for analyzing ionic structure according to the present disclosure, there is provided a collision cross sectional area determination method based on a Fourier transform equipment and time-frequency analysis, which enables ionic structure analysis, can be widely applied in an equipment based on Fourier transform, expands the detection ability of the Fourier transform equipment, and realizes non-destructive testing of the space dimension information of the sample ions. Based on the exact determination with respect to the space dimensions of the sample ions, isomers such as different conformations of the same protein can be distinguished, or complicated mixed samples having the same mass but different sizes can be detected through this method at a time, thus the detection efficiency of the sample ions is improved, and the detection cost is reduced.

New embodiments may be obtained by splitting and combining the characteristics of each embodiment mentioned above, which may not depart from the scope of the present invention. Moreover, various changes and modifications apparent to those skilled in the art may not deviate from the principle and scope of the present invention. Therefore, these changes and modifications shall also be included in the present invention as long as the changes and modifications fall within the scope of the appended claims and equivalent schemes.

What is claimed is:

1. A method for analyzing ionic structure, comprising the following steps of:

ion trapping and exciting step: applying a radio frequency electric field on a linear ion trap to trap sample ions in the linear ion trap, the applied radio frequency electric field having high order components which are even order fields; and applying an auxiliary alternating current electric field or applying a broadband excitation electric field on the linear ion trap to cause the sample ions to be excited to a motion amplitude not exceeding the trapping ability of the linear ion trap, the motion amplitude at this moment being recorded as a primary motion amplitude (a0) and the moment corresponding to the primary motion amplitude (a0) being recorded as a first moment (t0);

signal collecting step: continuously feeding carrier gas into the linear ion trap and keeping a degree of vacuum in the linear ion trap to be smaller than 1.333 Pa, the sample ions being collided with the carrier gas and the motion amplitude being decreased gradually till a second moment (tt), and collecting a time domain signal of an image current generated by the sample ions during the process from the first moment (t0) to the second moment (tt); and signal processing step: analyzing the time domain signal through a time-frequency analysis method and respectively obtaining time-varying characteristic curves (C) of the motion frequencies (f) of ions having various sizes in the sample ions varied with time so as to distinguish among the ions having different sizes, each of the time-varying characteristic curves (C) indicating a corresponding relation between a motion frequency of the ion having a corresponding size and a collision cross sectional area of the ion and the carrier gas.

2. The method according to claim 1, wherein after the signal processing step, the method further comprises a time domain signal filtering step: the time domain signal being filtered by a filter so as to obtain a less-interfered time domain signal.

3. The method according to claim 1, wherein the time-frequency analysis method in the signal processing step is selected from Fourier transform method, fast Fourier transform method, short time Fourier transform method, fractional Fourier transform method or wavelet analysis method.

4. The method according to claim 1, wherein in the signal processing step, the time-varying characteristic curve of the motion frequency (f) of the sample ion varied with time satisfies equation:

$$f_1 = f_0 \sqrt{1 + \frac{3a_1^2}{4}\epsilon_3 + \frac{5a_1^4}{8}\epsilon_5 + \frac{35a_1^6}{64}\epsilon_7 + \ldots} \quad (1)$$

where $a_1$ is a motion amplitude of the sample ion; $f_0$ is a motion frequency of the ion without a high order field; and $\epsilon_3$, $\epsilon_5$ and $\epsilon_7$ are even order field perturbation coefficients corresponding to the even order fields, and $$a_1 = \frac{1}{(1/a_0 + c)e^{\frac{\delta_1}{2}t} - c} \quad (2)$$

where $a_0$ is the primary motion amplitude of the sample;

$$c = \frac{8\delta_2\omega_0}{3\pi\delta_1}$$

is a constant;

$$\delta_1 = \frac{q\sqrt{\frac{\alpha_p(M+m)}{mM}}}{2\varepsilon_0} \frac{p}{Tk} \frac{M}{m+M}$$

is a Langevin decay coefficient;

$$\delta_2 = (\pi r^2)\frac{p}{Tk}\frac{M}{m+M}$$

is a hard-sphere decay coefficient; r is an effective radius of the sample ion; q is electric charge of the sample ion; αp is a polarizability; $\epsilon_0$ is a permittivity of vacuum; p is a degree of vacuum; T is a thermodynamic temperature; k is a Boltzmann constant; M is a mass of the carrier gas; and m is a mass of the sample ion;

substituting equation (2) into equation (1), thus obtaining a relation equation of the effective radius (r) of the sample ion and the motion frequency (f) of the sample ion varied with time.

5. The method according to claim 4, wherein the method further comprises the following step of:

drawing a relation curve of the effective radius (r) of the sample ion and the motion frequency (f) of the sample ion varied with time through a numerical method according to the relation equation of the effective radius (r) of the sample ion and the motion frequency (f) of the sample ion varied with time.

6. The method according to claim 1, wherein the method further comprises a signal analysis step:

obtaining corresponding characteristic values (S) by analyzing each time-varying characteristic curve (C) from the signal processing step, and establishing a corresponding relation between each characteristic value (S) and the collision cross sectional area of the ion having the corresponding size, thus determining a size relation between the ions having various sizes in the sample ions.

7. The method according to claim 6, wherein in the signal analysis step, with respect to each time-varying characteristic curve, the characteristic value (S) thereof is obtained through a following step:

connecting a motion frequency ($f_{t_0}$) point of the sample ion at the first moment ($t_0$) with a motion frequency ($f_{t_r}$) point of the sample ion at the second moment ($t_r$) to create a straight line (L), and integrating over a closed curve encircled by the straight line (L) and the time-varying characteristic curve (C) from the first moment ($t_0$) to the second moment ($t_r$) to obtain the characteristic value (S) of the time-varying characteristic curve.

8. The method according to claim 7, wherein in the signal processing step, the time-varying characteristic curve of the motion frequency (f) varied with time satisfies equation:

$$f_1 = f_0\sqrt{1 + \frac{3a_1^2}{4}\epsilon_3 + \frac{5a_1^4}{8}\epsilon_5 + \frac{35a_1^6}{64}\epsilon_7 + \ldots} \quad (1)$$

where $a_1$ is a motion amplitude of the sample ion; $f_0$ is a motion frequency of the ion without a high order field; and $\epsilon_3$, $\epsilon_5$ and $\epsilon_7$ are even order field perturbation coefficients corresponding to the even order fields, and $$a_1 = \frac{1}{(1/a_0 + c)e^{\frac{\delta_1}{2}t} - c} \quad (2)$$

where $a_0$ is the primary motion amplitude of the sample;

$$c = \frac{8\delta_2\omega_0}{3\pi\delta_1}$$

is a constant;

$$\delta_1 = \frac{q\sqrt{\frac{\alpha_p(M+m)}{mM}}}{2\varepsilon_0}\frac{p}{Tk}\frac{M}{m+M}$$

is a Langevin decay coefficient;

$$\delta_2 = (\pi r_0^2)\frac{p}{Tk}\frac{M}{m+M}$$

is a hard-sphere decay coefficient; $r_0$ is an effective radius of the sample ion; q is electric charge of the sample ion; $\alpha_p$ is a polarizability; $\epsilon_0$ is a permittivity of vacuum; p is a degree of vacuum; T is a temperature; k is a Boltzmann constant; M is a mass of the carrier gas; and m is a mass of the sample ion;

substituting equation (2) into equation (1), thus obtaining a relation equation of the effective radius ($r_0$) of the sample ion and the motion frequency (f) of the sample ion varied with time; and under a same measuring condition, respectively integrating over time (t) on both sides of the relation equation of the frequency (f) and the effective radius ($r_0$) of the sample ion, thus obtaining a corresponding relation between a characteristic value (S) and the effective radius ($r_0$) of the ion having a corresponding size.

* * * * *